US 8,158,170 B2
Apr. 17, 2012

(12) United States Patent
Kim et al.

(54) PHARMACEUTICAL COMPOSITION COMPRISING METADOXINE AND GARLIC OIL FOR PREVENTING AND TREATING ALCOHOL-INDUCED FATTY LIVER AND STEATOHEPATITIS

(75) Inventors: Sang Geon Kim, Seoul (KR); Sung Hwan Ki, Seoul (KR); Jae Hoon Choi, Cheonan (KR)

(73) Assignee: SNU R&DB Foundation, Seoul (KR)

( * ) Notice: Subject to any disclaimer, the term of this patent is extended or adjusted under 35 U.S.C. 154(b) by 356 days.

(21) Appl. No.: 12/516,968

(22) PCT Filed: Nov. 30, 2007

(86) PCT No.: PCT/KR2007/006162
§ 371 (c)(1),
(2), (4) Date: May 29, 2009

(87) PCT Pub. No.: WO2008/066353
PCT Pub. Date: Jun. 5, 2008

(65) Prior Publication Data
US 2010/0062090 A1 Mar. 11, 2010

(30) Foreign Application Priority Data
Nov. 30, 2006 (KR) .................. 10-2006-0119935

(51) Int. Cl.
A61K 36/8962 (2006.01)
(52) U.S. Cl. ........................................ 424/754
(58) Field of Classification Search .............. None
See application file for complete search history.

(56) References Cited

U.S. PATENT DOCUMENTS
3,636,203 A * 1/1972 Kopjas ............... 424/754

FOREIGN PATENT DOCUMENTS
| CN | 1159928 | * | 9/1997 |
| CN | 1385183 | * | 12/2002 |
| JP | 2006-248939 A | | 9/2006 |
| KR | 10-2005-0043091 A | | 5/2005 |
| KR | 10-2005-0043091 A | | 11/2005 |

OTHER PUBLICATIONS

Supplemental EU Search Report issued in EP 07 85 1168 dated Dec. 3, 2009.
Stickel, F., et al., "Alkoholische Lebererkrankung-Etablierte and experimentelle Therapieansatze," Zeitschrift Fuer Gastroenterologie, 41:4, pp. 333-342, Apr. 2003.
Yang, C.S. et al., "Mechanisms of Inhibition of Chemical Toxicity and Carcinogenesis by Diallyl Sulfide (DAS) and Related Compounds from Garlic," J. of Nutrition, pp. 1041S-1045S, 2001.
Ki, S.H., et al., "Combined metadoxine and garlic oil treatment efficaciously abrogates alcoholic steatosis and CYP2E1 induction in rat liver with restoration of AMPK activity," Chemico-Biological Interactions, 169, pp. 80-90, 2007.
Shimada M., et al., "Human hepatocytes are protected from ethanol-induced cytotoxicity by DADS via CYP2E1 inhibition," Toxicology Letters, 163:3, pp. 242-249, Jun. 2006.
Valil et al., "The therapeutic effect of metadoxine on alcoholic and non-alcoholic steatohepatitis," Orvosi Hetilap, 146:7, Nov. 20, 2005, pp. 2409-2414.
Masashi, Shinmada et al., "human hepatocytes are protected from ethanol-induced cytoxicity by DADS via CYP2E inhibition," Toxicology Letters, 163(2006), Dec. 2005, pp. 242-249.
Vali L. et al. "The therapeutic effect of metadoxine on alcoholic and non-alcoholic steatohepatitis" Orvosi Hetilap, Nov. 20, 2005, pp. 2409-14146(47).
Masashi Shimada et al. "Human hepatocytes are proteccted from ethanol-induced cytoxicity by DADS via CYP2E1 inhibition", Toxicology Letters, Dec. 13, 2005, pp. 242-249 163(2006).
Sparnins VL et al., "Effects of organosulfur compounds from garlic and onions on benzo[a]pyrene-induced neoplasia and gluthathione S-transferase activity in the mouse", Carcinogenesis, Jan. 1988, 9(1):131-4.
Arosio B et al., "Changes in expression of the albumin, fibronectin and type I procollagen genes in CCl4-induced liver fibrosis: effect of pyridoxol L, 2-pyrrolidon-5 carboxylate", Pharmacol Toxicol, Dec. 1993, 73(6):301-4.
Caballeria J. et al., "Metadoxine accelerates fatty liver recovery in alcoholic patients: results of a randomized double-blind, placebocontrol trial. Spanish Group for the Study of Alcoholic Fatty Liver", J Hepatol, Jan. 1998, 28(1):54-60.
Calabrese V. et al., "Long-term ethanol administration enhances age-dependent modulation of redox state in central and peripheral organs of rat: protection by metadoxine" Drugs Exp Clin Res., 1998, 24(2):85-91.
Calabrese V. et al., "Effects of metadoxine on cellular formation of fatty acid ethyl esters in ethanol treated rats", Int J Tissue React., 1995, 17(3):101-8.
Pablo Muriel et al., "Fibrosis and glycogen stores depletion induced by prolonged biliary obstruction in the rat are ameliorated by metadoxine", Liver International, 2003, 23, 262-268.
John F. Brady et al., "Effect of Diallyl Sulfide on Rat Liver Microsomal Nitrosamine Metabolism and Other Monooxygenase Activities", Cancer Research, Nov. 1, 1988, 48, 5937-5940.
Bandaru S. Reddy et al., "Chemoprevention of Colon Carcinogenesis by Organosulfur Compounds", Cancer Research, Aug. 1, 1993, 53, 3493-3498.

(Continued)

Primary Examiner — Christopher R. Tate
(74) Attorney, Agent, or Firm — Sughrue Mion, PLLC

(57) ABSTRACT

Provided is a pharmaceutical or food or drink composition for preventing or treating alcohol-induced fatty liver or steatohepatitis comprising metadoxine (pyridoxol 1-2-pyrrolidone-5-carboxylate) and garlic oil as active ingredients. The concurrent administration of metadoxine and garlic oil according to the present invention exhibits outstandingly superior effects of inhibiting the accumulation of triglyceride and increase of blood AST (aspartate aminotransferase) level in liver el tissue, inhibiting the expression of FAS (fatty acid synthase), CYP2E1 and iNOS (inducible nitric oxide synthase) and inhibiting the deactivation of AMPK (AMP-activated protein kinase), as compared to the administration of metadoxine or garlic oil only.

8 Claims, 9 Drawing Sheets

OTHER PUBLICATIONS

John F. Brady et al., "Inhibition of cytochrome P-450 2E1 by diallyl sulfide and its metabolites", Chem Res Toxicol, Nov.-Dec. 1991, 4(6):642-7.

Agarwal KC, "Therapeutic actions of garlic constituents", Med Res Rev, Jan. 1996, 16(1):111-24.

Augusti KT, "Therapeutic values of onion (*Allium cepa* L.) and garlic (*Allium sativum* L.)", Indian J Exp. Biol., Jul. 1996, 34(7):634-40.

Hayes MA et al., "Inhibition of hepatocarcinogenic responses to 1,2-dimethylhydrazine by diallyl sulfide, a component of garlic oil", Carcinogenesis, 8(8):1155-7, Aug. 1987.

International Search Report, dated Jan. 30, 2008.

* cited by examiner

[Figure 1]
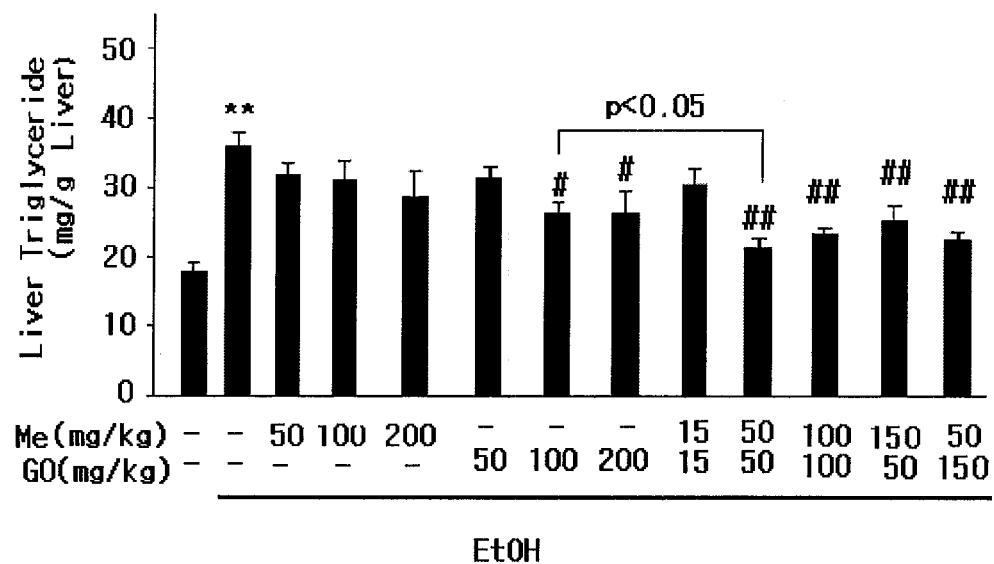
[Figure 2]
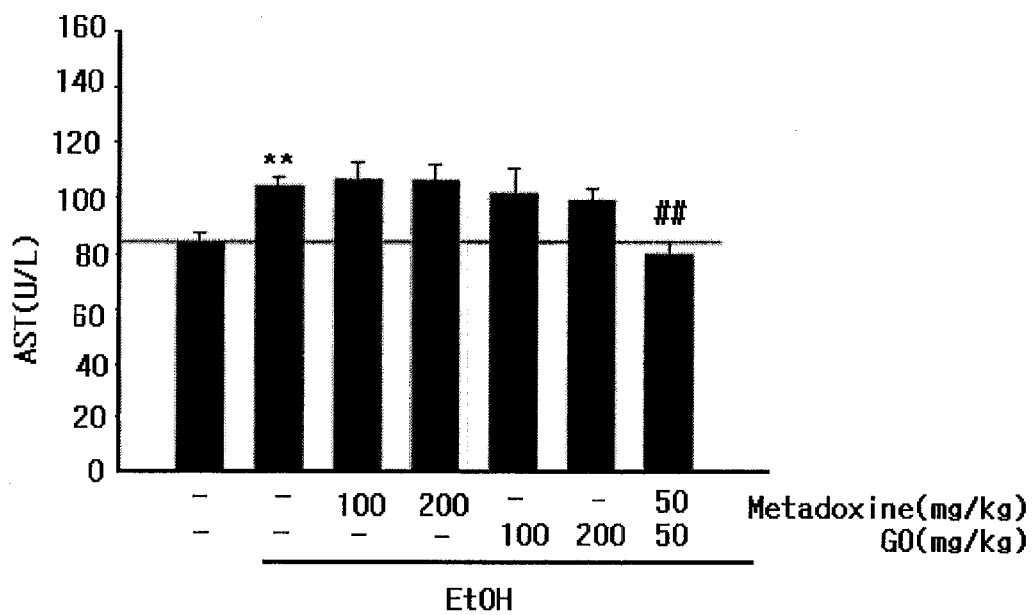

[Figure 3]
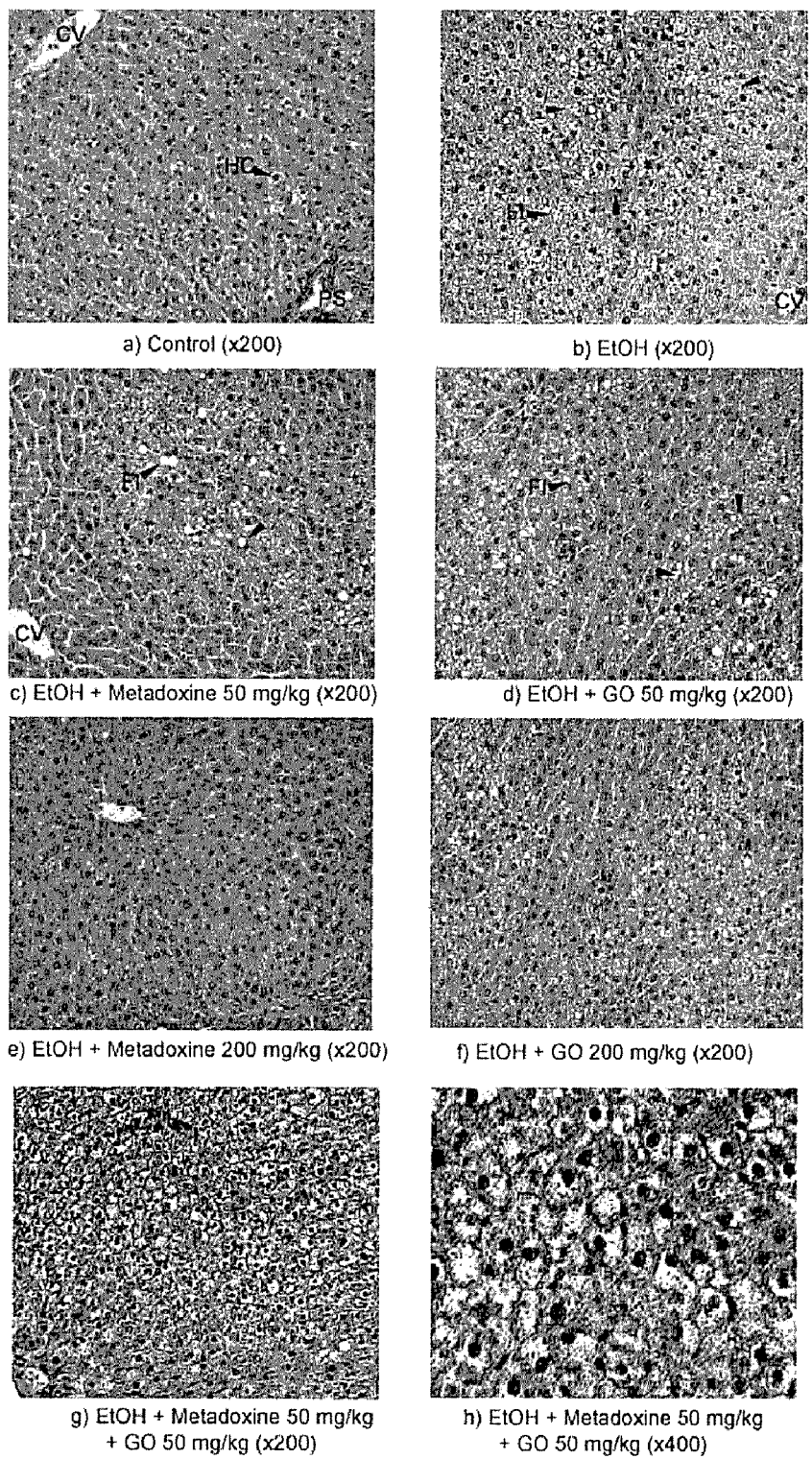

[Figure 4]
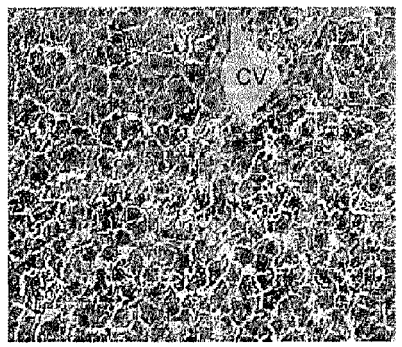
a) Control (X200)
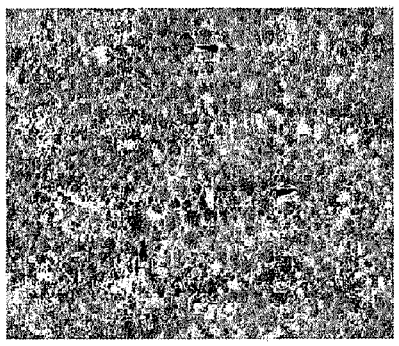
b) EtOH (x200)
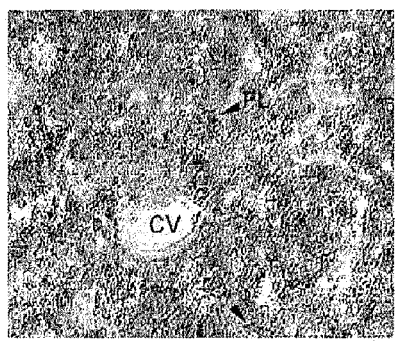
c) EtOH+ Metadoxine 50 mg/kg (x200)
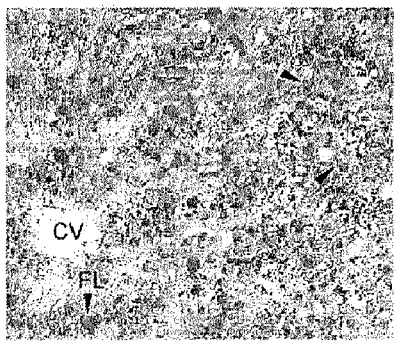
d) EtOH+ GO 50 mg/kg (x200)
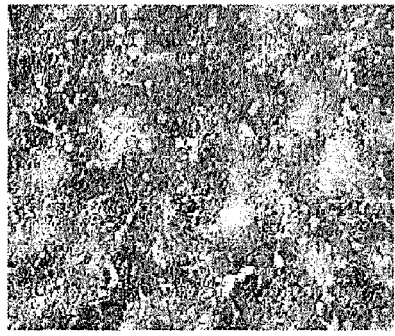
e) EtOH+ Metadoxine 200 mg/kg
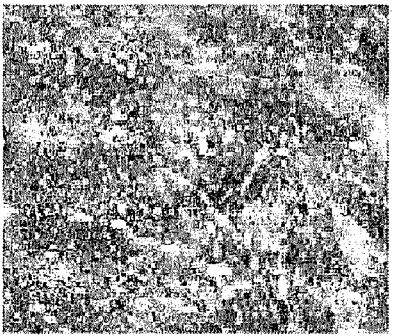
f) EtOH+ GO 200 mg/kg
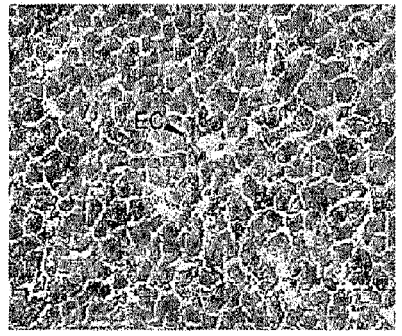
g) EtOH+ Metadoxine 50 mg/kg+ GO 50 mg/kg (x200)

[Figure 5]
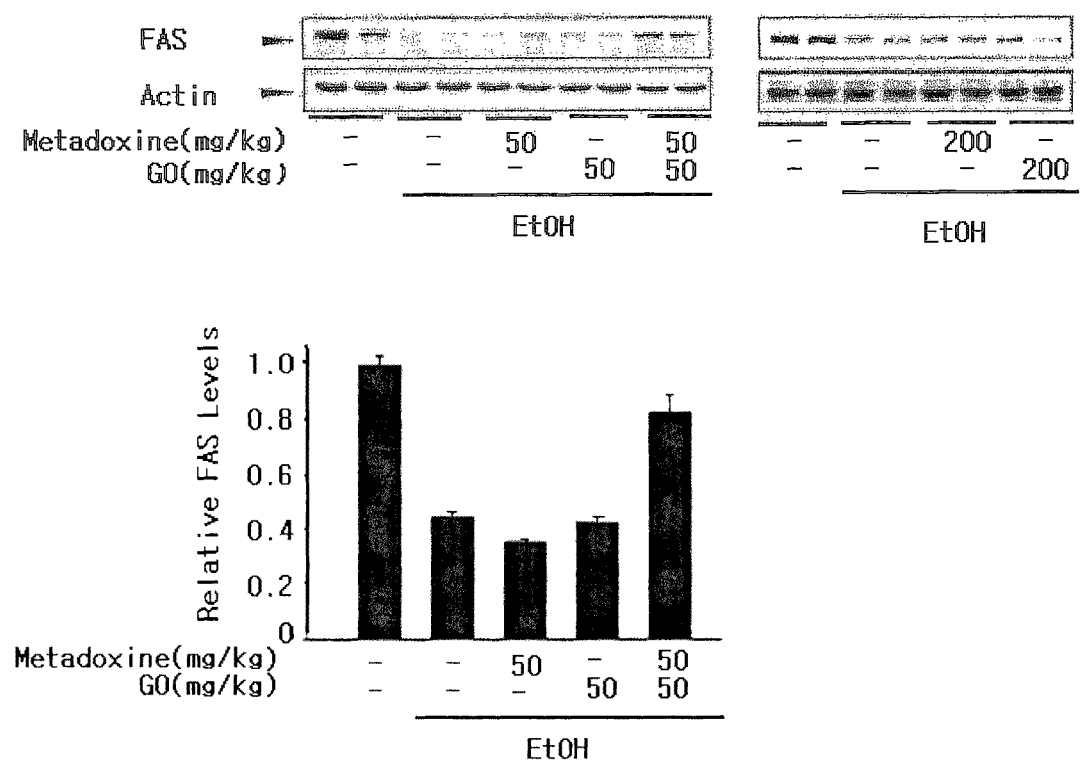

[Figure 6]
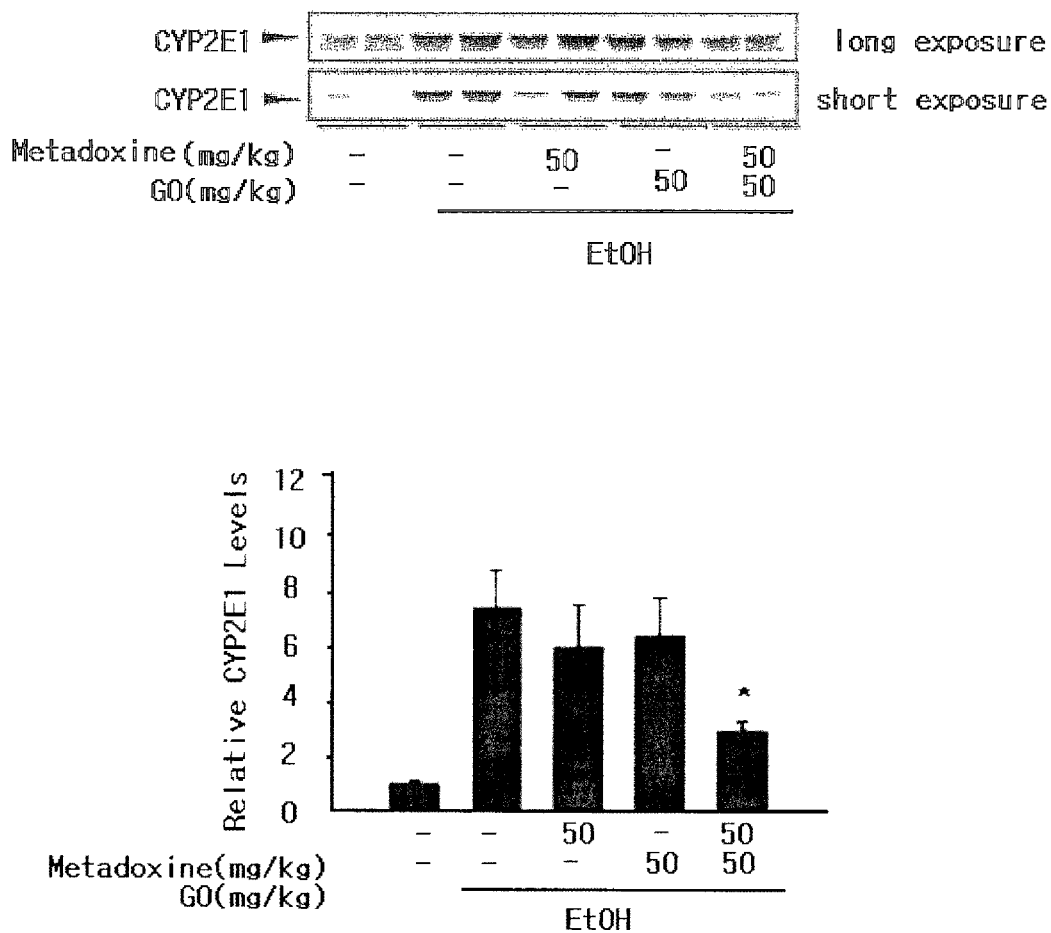

[Figure 7]
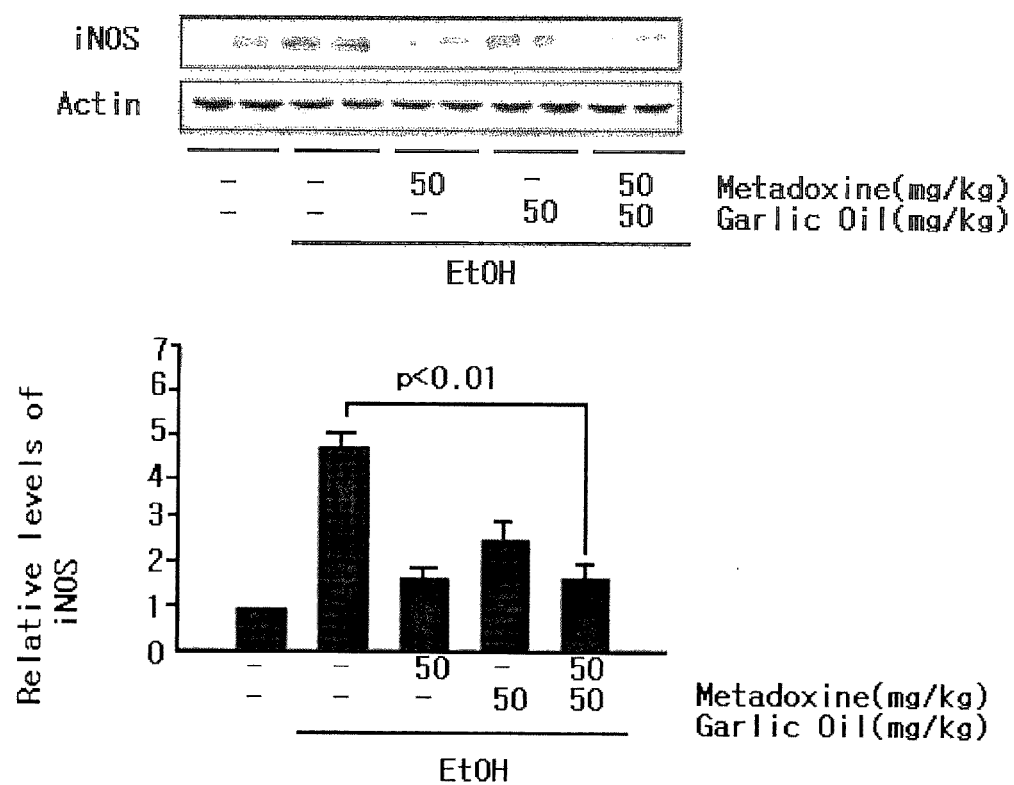

[Figure 8]
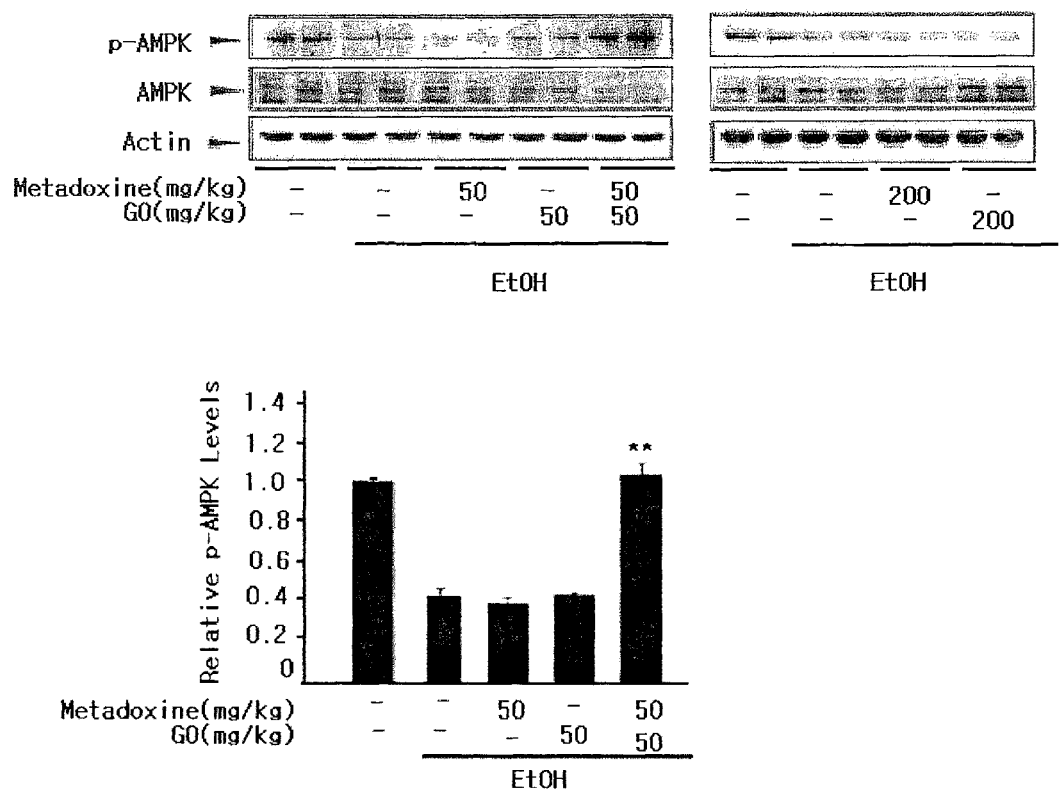

[Figure 9]
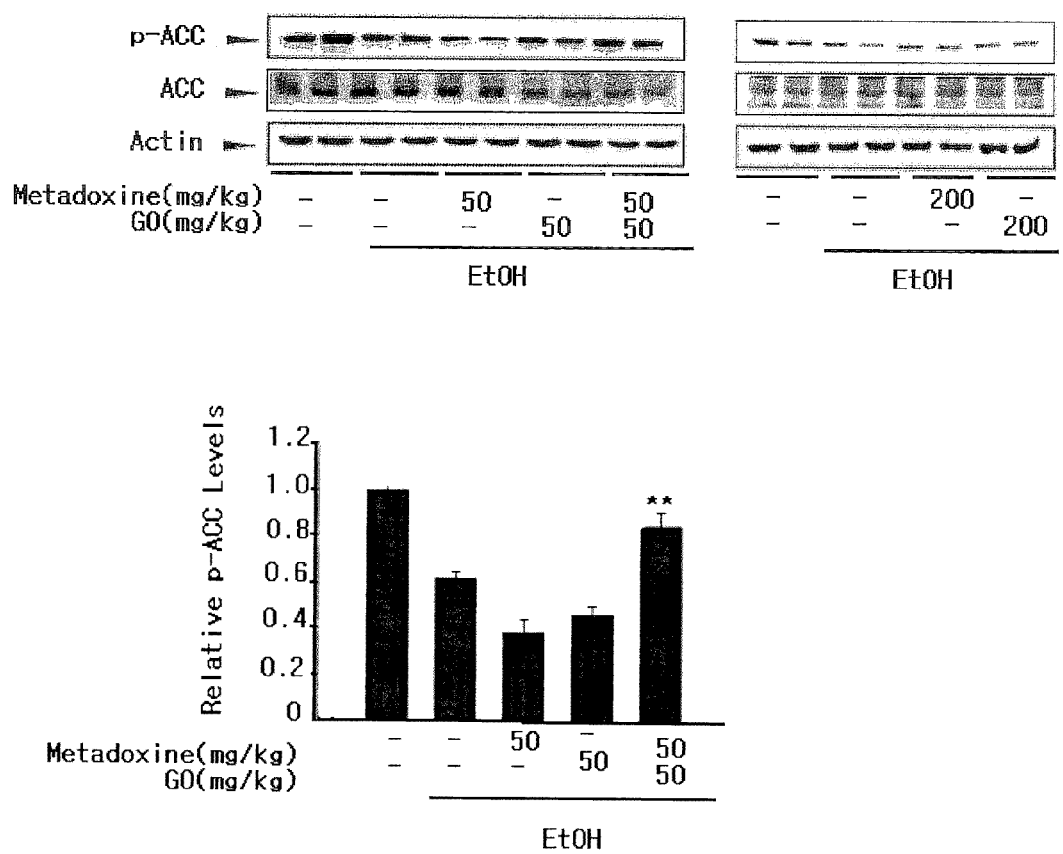

[Figure 10]
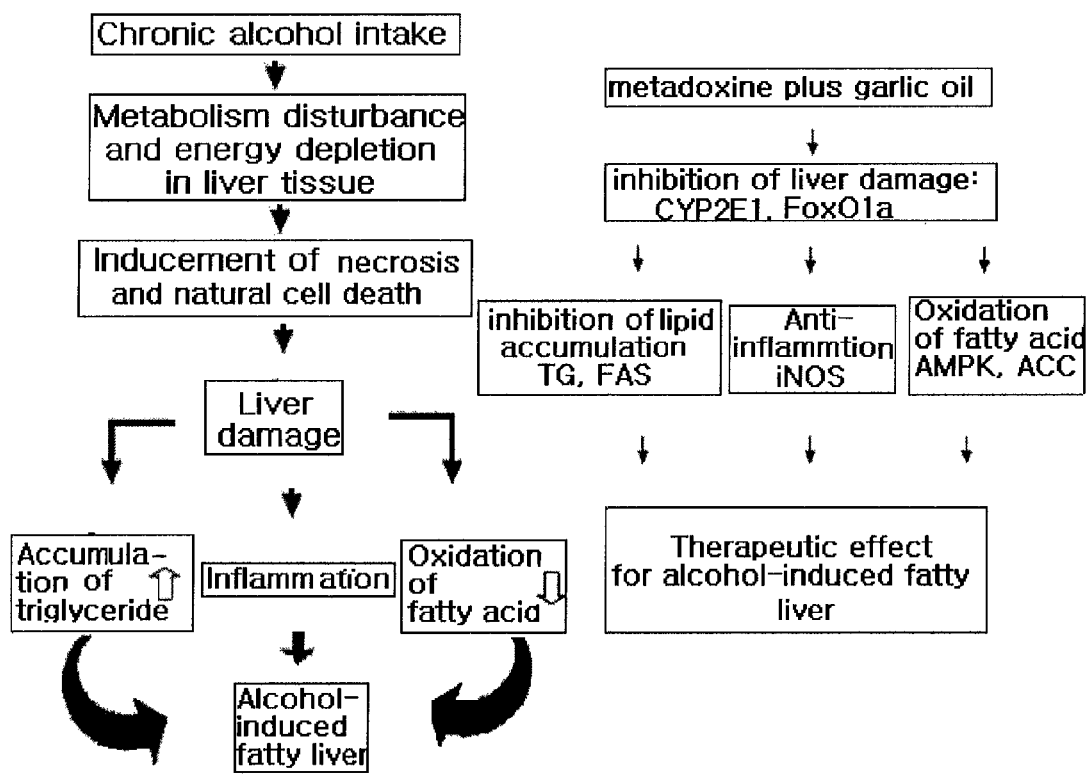

PHARMACEUTICAL COMPOSITION COMPRISING METADOXINE AND GARLIC OIL FOR PREVENTING AND TREATING ALCOHOL-INDUCED FATTY LIVER AND STEATOHEPATITIS

This is a national stage application under 35 U.S.C.§371 of PCT/KR2007/006162 filed Nov. 30, 2007, which claims priority from Korean patent application 10-2006-0119935 filed on Nov. 30, 2006, all of which are incorporated herein by reference.

TECHNICAL FIELD

The present invention relates to a pharmaceutical composition for treating alcohol-induced fatty liver or steatohepatitis comprising metadoxine and garlic oil as active ingredients.

BACKGROUND ART

Fatty liver refers to a pathogenic condition where fat comprises more than 5% of the total weight of the liver. Liver diseases including the fatty liver, hepatitis, fibrosis and cirrhosis are known to be the most serious disease next to cancer causing death in people with ages 40 to 50, in the advanced countries. In advanced countries, nearly about 30% of the population is with fatty liver, and about 20% of people with fatty liver progresses to cirrhosis. About half of the cirrhosis patients die of liver diseases within 10 years after the diagnosis. Fatty liver and steatohepatitis are frequently found in people who intake excessive alcohols and who have obesity, diabetes, hyperlipemia, etc. Among them, alcoholic steatohepatitis (ASH), which is caused by excessive alcohol intake, is at high risk of progressing to hepatitis, cirrhosis and hepatoma, along with non-alcoholic steatohepatitis (NASH).

When taken in, alcohol is carried to the liver and oxidized to acetaldehyde by such enzymes as alcohol dehydrogenase, catalase, etc. The acetaldehyde is metabolized and converted into acetate and is used as energy source. Repeated alcohol intake induces the increase of NADH and $NADP^+$ during the metabolism and acetaldehyde which as the metabolite product of alcohol depletes GSH, thereby changing intracellular oxidation-reduction homeostasis and inducing oxidative stress. Oxidative stress may cause mitochondrial dysfunction, lipid peroxidation and protein modification, thereby leading to death of hepatocytes, inflammation, activation of astrocytes, and the like. In addition, the increase of NADH promotes lipid synthesis, thereby inducing fatty liver.

At present, there are few therapeutically effective drugs for treating fatty liver. Exercise and controlled diet are recommended, but these are not so effective in treating fatty liver. The development of an effective treatment drug is in desperate need. As it is known that fatty liver is related with insulin resistance which is found in diabetes and obesity, the therapeutic effect of some anti-diabetic drugs, e.g., metformin, on fatty liver has been reported. But, the drug has the problem that it may induce adverse reactions such as hepatotoxicity or lactic acidosis. Betaine, glucuronate, methionine, choline and lipotrophic agents are often used as alternative supplementary drug therapy, but they are not fully proven on medical or pharmaceutical basis. Accordingly, development of a fatty liver treatment having superior effect and safety with no adverse reactions is in need.

Metadoxine (pyridoxol 1-2-pyrrolidone-5-carboxylate) is a complex compound of pyridoxine and pyrrolidone carboxylate represented by the formula (1) below:

[Chemistry Figure 1]

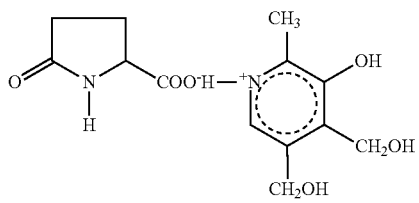

Metadoxine is a drug used to treat alcoholic liver disease. It is used to treat liver fibrosis and fatty liver through increasing alcohol metabolism and turnover, reducing toxicity of free radicals and restoring the level of ATP and glutathione (Arosio, et al., *Pharmacol. Toxicol.* 73: 301-304, 1993; Calabrese, et al., *Int. J. Tissue React.* 17: 101-108, 1995; Calabrese, et al., *Drugs Exp. Clin. Res.* 24: 85-91, 1998; Caballeria, et al., *J. Hepatol.* 28: 54-60, 1998; and Muriel, et al., *Liver Int.* 23: 262-268, 2003).

However, metadoxine is unable to inhibit the expression and activation of alcohol-induced cytochrome P4502E1 (CYP2E1), which is a key enzyme involved in alcohol-induced toxicity, and thus unable to control the augmentation of inflammation mediated by CYP2E1. Therefore, the treatment of alcohol-induced fatty liver using metadoxine is very limited. Further, the expression of CYP2E1 is related with insulin resistance, thus metadoxine cannot not overcome insulin resistance.

Garlic oil is a liquid including about 1% of allicin along with reduced allicin and other sulfur-containing substances. Upon binding to vitamin $B_1$, allicin is turned into allithiamin, which is chemically stable, acts swiftly, and is easily absorbed by the digestive organs. The substance inhibits carcinogenesis induced by chemicals in white rats (Brady, et al., *Cancer Res.* 48: 5937-5940, 1988; and Reddy, et al., *Cancer Res.* 53: 3493-3498, 1993), induces phase II enzyme (Hayes, et al., *Carcinogenesis* 8: 1155-1157, 1987; and Sparnins, et al., *Carcinogenesis* 9: 131-134, 1988), and inactivates CYP2E1 (Brady, et al., *Chem. Res. Toxicol.* 4:642-647, 1991). In addition, garlic oil is reported to have antithrombotic, anti-atherosclerotic, antimutagenic, anticancer and antibacterial activities (Agarwal, *Med. Res. Rev.* 16: 111-124, 1996; and Augusti, *Indian J. Exp. Biol.* 34: 634-660, 1996).

DISCLOSURE

The present inventors studied various composite compositions comprising drugs with different therapeutic paths in order to effectively treat alcoholic steatohepatitis and prevent hepatitis caused by fatty liver. As a result, the present inventors found out that, when metadoxine, which is effective in promoting excretion of alcohol and acetaldehyde and inhibiting toxicity induced by free radicals, and garlic oil, which has CYP2E1 inhibition activity and is effective in preventing the damage of hepatocytes by chemicals, are administered concurrently with optimal proportion, an synergistically and outstandingly improved preventive and therapeutic effect can be attained for alcohol-induced fatty liver and steatohepatitis caused thereby than when the substances are administered alone.

Accordingly, an object of the present invention is to provide a composition for preventing and treating alcohol-induced fatty liver and steatohepatitis comprising metadoxine and garlic oil with optimal proportion as active ingredients.

Another object of the present invention is to provide a composition for improving or restoring liver function damaged by alcohol intake comprising metadoxine and garlic oil with optimal proportion as active ingredients.

In order to attain the objects, the present invention provides a pharmaceutical composition for preventing or treating alcohol-induced fatty liver and steatohepatitis or a pharmaceutical composition for improving or restoring liver function comprising metadoxine represented by the formula (1) below and garlic oil as active ingredients and further comprising a pharmaceutically acceptable excipient. Further, the present invention provides a food or drink composition for inhibiting, preventing or ameliorating alcohol-induced fatty liver and steatohepatitis or improving or restoring liver function comprising metadoxine represented by the formula (1) below and garlic oil as active ingredients and further comprising a sitologically acceptable excipient.

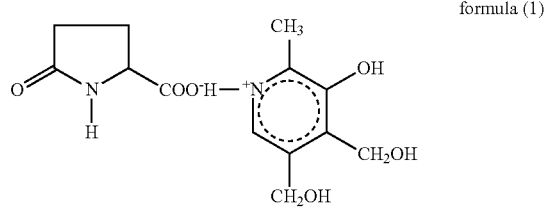

formula (1)

A feature of the composition of the present invention is that the concurrent administration of metadoxine and garlic oil provides outstandingly improved synergical effect of preventing and treating alcohol-induced fatty liver and steatohepatitis and restoring and improving liver function than when each of the substances is administered alone.

The present inventors administered metadoxine and garlic oil alone or concurrently with various proportions and dosages to rats fed an alcohol diet in fatty liver model, and verified pharmacological effect on alcohol-induced fatty liver, in order to find the combination giving the optimal therapeutic effect. During the concurrent administration, the mixing proportions of metadoxine to garlic oil were 1:1, 1:2, 2:1, 1:3 and 3:1, based on weight.

The rats fed an alcohol diet for 4 weeks exhibited significantly increased triglyceride level in liver tissue and significantly increased blood AST level, an indication of hepatotoxicity, as compared to the control group. In contrast, the metadoxine/garlic oil administered group exhibited significantly reduced tissue triglyceride level and blood AST level (see FIGS. 1 and 2). This coincides with the histological analysis result of specific staining of fat in liver tissue (see FIGS. 3 and 4).

The expression of FAS in liver tissue, which was reduced by the chronic alcohol intake, was not affected by the administration of either metadoxine or garlic oil, even at high dosage. But, surprisingly, it was restored to normal level when the two were administered concurrently (see FIG. 5). The expression of CYP2E1 participating in alcohol metabolism, which increased significantly in fatty liver induced by alcohol, also decreased remarkably and was restored to normal level when the metadoxine/garlic oil composition of the present invention was administered (see FIG. 6).

The expression of iNOS, which is a strong inflammation inducing enzyme in liver tissue and is believed to contribute to liver damage, is strongly induced by chronic alcohol intake. The expression of iNOS decreased by the administration of metadoxine, but was not affected by the administration of garlic oil. When metadoxine and garlic oil were administered concurrently with an optimal proportion, the expression of iNOS decreased remarkably (see FIG. 7). The activities of AMPK, which is a key enzyme involved in the oxidation of fatty acid, and its substrate ACC were examined. When metadoxine or garlic oil was administered alone, the activities of AMPK and ACC in liver tissue, which decreased due to alcohol intake, were not restored at all. However, surprisingly, they were restored to normal level when metadoxine and garlic oil were administered concurrently (see FIGS. 8 and 9).

The therapeutic effect was outstanding when the mixing proportion of metadoxine to garlic oil was from 1:1 to 1:3 or from 1:1 to 3:1, preferably at 1:1.

These experimental results confirm that, when the two substances are administered concurrently, alcohol-induced fatty liver and steatohepatitis are inhibited unexpectedly or synergically, as compared to when they are administered alone. Further, since the concurrent administration of metadoxine and garlic oil in accordance with the present invention provides superior effect of inhibiting triglyceride level and hepatotoxicity, as compared to the administration of metadoxine only at high dosage, it is expected to reduce side reactions (e.g., peripheral neuropathy) that may be caused by excessive or extended administration of metadoxine. From these results, it is expected that the synergic effect of the promoted alcohol metabolism by metadoxine and the antioxidative, anti-inflammatory and CYP2E1 inhibiting effects by garlic oil will maximize the preventive and therapeutic effect for fatty liver and steatohepatitis (see FIG. 10).

Accordingly, the composition comprising metadoxine and garlic oil as active ingredients according to the present invention can provide superior effect of treating alcohol-induced fatty liver and restoring liver function and is applicable for clinical uses with few side reactions.

Preferably, the pharmaceutical composition of the present invention is administered by preparing each substance into separate preparation form or combining the two into a single preparation form. The composition may be administered orally by preparing into a preparation form for oral administration according to a method commonly employed in the art. Such preparation form for oral administration includes hard and soft capsule, tablet, powder, suspension, syrup, injection, and the like. In addition to the two active ingredients, the preparation form for oral administration may further include one or more commonly used pharmaceutically inactive excipient, for example, a filler such as starch, lactose, carboxymethylcellulose, kaolin, etc., a binder such as water, gelatin, alcohol, glucose, gum arabic, gum tragacanth, etc., a disintegrant such as starch, dextrin, sodium alginate, etc. or a lubricant such as talc, stearic acid, magnesium stearate, liquid paraffin, etc. The pharmaceutical composition of the present invention may further include a solubilizer for facilitating dissolution.

The pharmaceutical composition of the present invention also may be administered non-orally, for example by subcutaneous injection, intravenous injection, intramuscular injection or intracardiac injection. A preparation form for non-oral administration is prepared by mixing metadoxine and garlic oil with a stabilizer or a buffer in water to obtain a solution or suspension and putting the same in an ampule or a vial.

A daily dosage of the composition according to the present invention depends on various factors such as severity of fatty liver, age of patient, physical conditions, complications, and so forth. Typically, based on grown-ups, the composition comprising metadoxine and garlic oil is administered at a dose from 15 mg to 2 g, preferably from 50 mg to 1 g, once a day or twice a day by splitting into two doses. However, in patients with severe fatty liver or steatohepatitis, the composition of the present invention may be administered at a larger dose. Most preferably, a unit dose including 250 mg of metadoxine and 250 mg of garlic oil is orally administered once or twice a day.

Through optimized combination of the promotion of alcohol metabolism offered by metadoxine and the superior antioxidative, anti-inflammatory and CYP2E1 inhibiting effects offered by garlic oil, the pharmaceutical composition according to the present invention effectively inhibits the progress of alcohol-induced fatty liver and steatohepatitis, with little toxicity and few side reactions.

Further, the present invention provides a food additive or drink composition for inhibiting and preventing alcohol-induced fatty liver and steatohepatitis comprising metadoxine and garlic oil as active ingredients. The composition may also be used to recover or improve liver function.

In case metadoxine and garlic oil are used as food additives, they may be added directly or along with other foods or food ingredients. The amount of the active ingredients may be adequately determined depending on purposes (preventive, health promoting or therapeutic). Normally, metadoxine and garlic oil may be added to such food or drink in an amount from 0.0001 to 10 weight %, preferably from 0.1 to 5 weight %. In case of long-term intake for the purpose of health or hygiene improvement, a smaller amount may be selected. However, since the active ingredients are without safety problem, a larger amount can be selected, too.

The kind of food is not particularly limited. Examples of food to which metadoxine and garlic oil can be added include meat, sausage, bread, chocolate, candy, snack, confectionery, pizza, instant noodle, other noodles, gum, dairies including ice cream, soup, beverage, tea, drinks, alcoholic drinks, vitamin complex, and so forth.

DESCRIPTION OF DRAWINGS

FIG. 1 compares triglyceride level in liver tissue of rats in alcohol (EtOH)-induced fatty liver animal model, when metadoxine and garlic oil were administered alone or concurrently. ** indicates that the p-value was less than 0.01 as compared to the vehicle group, and # and ## indicate that the p-values were less than 0.05 and 0.01, respectively, as compared to the alcohol administered group.

FIG. 2 compares blood AST level of rats in alcohol (EtOH)-induced fatty liver animal model, when metadoxine and garlic oil were administered alone or concurrently. ** indicates that the p-value was less than 0.01 as compared to the vehicle group, and # and ## indicate that the p-values were less than 0.05 and 0.01, respectively, as compared to the alcohol administered group.

FIG. 3 shows the liver tissues of rats in alcohol-induced fatty liver animal model stained with hematoxylin and eosin (H&E), when metadoxine and garlic oil were administered alone or concurrently. CV stands for central vein, HC for hepatocyte and FI for fat infiltration (Me=metadoxine, GO=garlic oil).

FIG. 4 shows the liver tissues of rats in alcohol-induced fatty liver animal model stained with Oil Red O, which is used for specific staining of fats, when metadoxine and garlic oil were administered alone or concurrently. CV stands for central vein, HC for hepatocyte, FI for fat infiltration and EC for empty cytoplasm (Me=metadoxine, GO=garlic oil).

FIG. 5 compares the expression of fatty acid synthase (FAS) in liver tissue of rats in alcohol-induced fatty liver animal model, when metadoxine and garlic oil were administered alone or concurrently. ** indicates that the p-value was less than 0.01 as compared to the alcohol administered group.

FIG. 6 compares the expression of alcohol-induced cytochrome P4502E1 (CYP2E1) in liver tissue of rats in alcohol-induced fatty liver animal model, when metadoxine and garlic oil were administered alone or concurrently. * indicates that the p-value was less than 0.05 as compared to the alcohol administered group.

FIG. 7 compares the expression of inducible nitric oxide synthase (iNOS) in liver tissue of rats in alcohol-induced fatty liver animal model, when metadoxine and garlic oil were administered alone or concurrently.

FIG. 8 compares the enzymatic activity of AMP-activated protein kinase (AMPK) in liver tissue of rats in alcohol-induced fatty liver animal model, when metadoxine and garlic oil were administered alone or concurrently. ** indicates that the p-value was less than 0.01 as compared to the alcohol administered group.

FIG. 9 compares the enzymatic activity of acetyl-CoA carboxylase (ACC), which is a substrate of AMPK, in liver tissue of rats in alcohol-induced fatty liver animal model, when metadoxine and garlic oil were administered alone or concurrently. ** indicates that the p-value was less than 0.01 as compared to the alcohol administered group.

FIG. 10 schematically illustrates the mechanism leading to alcohol-induced fatty liver and the therapeutic effect of a drug comprising metadoxine and garlic oil.

MODE FOR INVENTION

Hereinafter, the present invention will be described in further details through examples. However, the following examples are only for the understanding of the present invention and they do not limit the present invention.

EXAMPLES

Test Animals and Diets

Male Sprague-Dawley rats (average body weight=140 to 160 g) purchased from Samtako (Osan, Korea) were used as test animals. Before testing, the rats were accustomed under the condition of humidity 55±5% and temperature 22±2° C. in the animal research facility of the College of Pharmacy, Seoul National University for at least 1 week. Lighting was changed at 7 a.m. and 7 p.m. on a 12-hour period basis. During the experiment, no significant change was observed in the consumption of feed or drinking water. Body weight and physical condition of the animals were examined every week, and Lieber-DeCarli liquid diet was supplied every day.

Rats randomly divided into 3 groups were treated as follows: (A) Normal diet (control diet) was given for 4 weeks and metadoxine dissolved in 40% polyethyleneglycol 400, Garlic Oil suspended in corn oil was orally administered for the last week. (B) Alcohol diet (ethanol diet) calorie-corrected for the normal diet was given for 4 weeks and metadoxine dissolved in 40% polyethyleneglycol 400, Garlic Oil suspended in corn oil was orally administered for the last week. (C) Alcohol diet (ethanol diet) calorie-corrected for the normal diet was given for 4 weeks and metadoxine and garlic oil were orally administered for the last week with a proportion from 1:1 to 1:3 or from 1:1 to 3:1, based on weight. Each group consisted of 10 rats.

The Lieber-DeCarli liquid diet was purchased from Dyets, Inc. (Bethlehem, Pa.). The normal diet had a caloric density of 1 kcal/mL (carbohydrate 65%, protein 20% and fat 15%). The ethanol diet was calorie-corrected for the normal diet by replenishing ethanol instead of maltose dextrin. The diets were stored in dark and cool place.

TABLE 1

Composition of Lieber-DeCarli diet (g/L)

| Composition | Normal diet | Ethanol diet |
|---|---|---|
| Casein | 41.40 | 41.40 |
| DL-Methionine | 0.30 | 0.30 |
| L-Cystine | 0.50 | 0.50 |
| Cellulose | 10.00 | 10.00 |
| Maltose dextrin | 115.20 | 25.60 |
| Corn oil | 8.50 | 8.50 |
| Olive oil | 28.40 | 28.40 |
| Safflower oil | 2.70 | 2.70 |
| Mineral mix | 8.75 | 8.75 |
| Vitamin mix | 2.50 | 2.50 |
| Choline bitartrate | 0.53 | 0.53 |
| Xanthan gum | 3.00 | 3.00 |
| Ethanol | — | 45.50 |

Sample Preparation

Metadoxine and garlic oil were obtained from Auspure Biotechnology (Shanghai, China), and the alcohol diet for inducing fatty liver was purchased from Dyet Co. (USA). Metadoxine and garlic oil were diluted to wanted concentrations with water and cooking oil.

Western Blot

Sodium dodecyl sulfate-polyacrylamide gel electrophoresis (SDS-PAGE) was carried out using Mighty Small II SE 250 apparatus according to the Laemmli UK method (1970). Lysis fraction of liver tissue was diluted in a sample dilution buffer [63 mM Tris (pH 6.8), 10% glycerol, 2% SDS, 0.0013% bromophenol blue, 5% β-mercaptoethanol] and electrophoresis was performed in an electrode buffer (15 g of Tris, 72 g of glycine and 5 g of SDS in 1 L) using 7.5% and 9% gel. After electrophoresis, proteins were transferred to nitrocellulose paper at 190 mAmps for a duration of 1 hour, using a transfer buffer [25 mM Tris, 192 mM glycine, 20% v/v methanol (pH 8.3)]. Anti-fatty acid synthase, anti-iNOS, anti-phospho AMPK-α anti-phospho ACC, anti-Fox01, anti-Fox03 and anti-CYP2E1 were reacted as primary antibodies. Then, horseradish peroxidase-conjugated goat anti-rabbit IgG and horseradish peroxidase-conjugated goat anti-mouse IgG were reacted for 1 hour as second antibodies, and the proteins were visualized using an ECL chemiluminescence system (Amersham, Gaithesberg, Mass.). Equal protein loading was confirmed by β-actin immunoblotting using anti-β-actin antibody (Sigma, St. Louis, Mo.). Change in the expression of proteins was analyzed by determining the color intensity of blots through densitometry. Densitometry scan was performed using Image Scan & Analysis System (Alpha-Innotech Co.). AlphaEase™ version 5.5 software was used and the background was omitted in the intensity calculation.

Analysis

Analysis was carried out using a pharmacological computational software. Significance among test groups was examined by the linear square method (Fisher R A, *Statistical Methods for Research Workers*, Edinburgh: Oliver & Boyd, 1925). Evaluation was performed by Newman-Keuls method (Norman G R, et al., *Biostatistics: The Bare Essentials,* 2000) (* stands for p<0.5, ** stands for p<0.01).

Example 1

Effect of Concurrent Oral Administration of Metadoxine and Garlic Oil on Triglyceride Level in Fatty Liver Tissue Alcohol diet was suspended in alcohol and water, such that the alcohol accounted for 37% of the total calorie and administered to rats for 4 weeks to establish a fatty liver animal model. Induction of fatty liver was identified through hermatological and histological analyses. 3 weeks after the administration of the alcohol diet, metadoxine (50, 100, 150 or 200 mg/kg body weight) and garlic oil (50, 100, 150 or 200 mg/kg) were orally administered every day alone or concurrently (metadoxine:garlic oil=1:1, 1:2, 2:1, 1:3 and 3:1) for a week, along with the alcohol diet. 24 hours after the final administration, blood and liver tissue were taken.

Triglyceride level in liver tissue is an index of fatty liver. After administering metadoxine and garlic oil alone or concurrently, triglyceride level in liver tissue was determined. The triglyceride level in liver tissue was remarkably lower when metadoxine and garlic oil were administered concurrently, than when they were administered alone (FIG. 1).

After administering metadoxine and garlic oil alone or concurrently, therapeutic effect on alcohol-induced fatty liver was analyzed histopathologically by H&E staining. Liver tissue was fixed in 10% neutral formalin solution and, following normal fixation and dehydration, was embedded with paraffin. The embedded tissue was sliced to a thickness of 4 µm and observed with an optical microscope after H&E staining. Microvesicular and macrovesicular steatosis was observed. As in the effect on triglyceride level, the concurrent administration of metadoxine and garlic oil exhibited remarkable effect in inhibiting accumulation of fat, as compared to when each substance was administered alone at high dose (FIG. 3). The analysis performed after staining with Oil Red O, which specifically stains accumulated fat in liver tissue, also showed that the concurrent administration of metadoxine and garlic oil provides outstanding synergic therapeutic effect against lipid accumulation caused by long-term alcohol intake (FIG. 4).

Example 2

Effect of Concurrent Oral Administration of Metadoxine and Garlic Oil on Blood AST Level Rats fed alcohol diet for 4 weeks showed significantly increased blood AST (aspartate aminotransferase) level, which is an index of hepatotoxicity, as compared to the control group. In contrast, the concurrent metadoxine/garlic oil administration group exhibited significantly decreased AST level (FIG. 2).

Example 3

Effect of Concurrent Oral Administration of Metadoxine and Garlic Oil on FAS Level in Fatty Liver Tissue Various molecular and cellular indices were examined in order to elucidate the outstanding synergic therapeutic effect on alcohol-induced fatty liver by concurrent administration of metadoxine and garlic oil. Expression of fatty acid synthase (FAS) in the liver tissue taken in Example 1 was analyzed by Western blotting. The decreased expression of FAS was not restored by the administration of metadoxine or garlic oil alone at high dose. In contrast, unexpectedly, it was restored to normal level when metadoxine and garlic oil were administered concurrently (FIG. 5).

Example 4

Effect of Concurrent Oral Administration of Metadoxine and Garlic Oil on CYP2E1 Level in Fatty Liver Tissue The expression of the alcohol metabolizing enzyme CYP2E1 in the liver tissue taken in Example 1 was analyzed by Western blotting. The increased expression of CYP2E1 caused by chronic alcohol intake significantly decreased and was restored to normal level when metadoxine and garlic oil were administered concurrently (FIG. 6).

Example 5

Effect of Concurrent Oral Administration of Metadoxine and Garlic Oil on iNOS Level in Fatty Liver Tissue iNOS is an enzyme strongly inducing inflammation in liver tissue. The induction of the expression of iNOS is considered as a primary mechanism of alcohol-induced liver damage (Mckim, et al., *Gastroenterology* 125:1834-1844, 2003; and Venkatraman A, et al., *Hepatology* 40: 565-573, 2004). The expression of iNOS in the liver tissue taken in Example 1 was analyzed by Western blotting. The expression of iNOS, which was strongly induced by the chronic alcohol intake decreased when metadoxine was administered alone, but no significant decrease was observed when garlic oil was administered alone. In the test group to which metadoxine and garlic oil were administered concurrently, the expression of iNOS decreased remarkably (FIG. 7).

Example 6

Effect of Concurrent Oral Administration of Metadoxine and Garlic Oil on AMPK and ACC Levels in Fatty Liver Tissue The levels of AMPK (AMP-activated protein kinase), a critical enzyme involved in the oxidation of fatty acid, and phosphate form of ACC (acetyl-CoA carboxylase), a substrate of AMPK, in the liver tissue taken in Example 1 were analyzed by Western blotting. As seen in FIGS. 8 and 9, the activities of AMPK and ACC, which decreased due to the alcohol intake, showed no change when either metadoxine or garlic oil was administered alone. In contrast, they were restored to normal levels when metadoxine and garlic oil were administered concurrently.

From these results, it was confirmed that the concurrent administration of metadoxine and garlic oil according to the present invention is effective in inhibiting the expression of CYP2E1, which induces liver damage, FAS, which is involved in lipid accumulation, and iNOS, which induces inflammation, while inducing the activation of AMPK and ACC, which play critical roles in the oxidation of fatty acid. Therefore, the concurrent administration of metadoxine and garlic oil according to the present invention provides outstanding therapeutic effect for alcohol-induced fatty liver and steatohepatitis (FIG. 10).

Various preparation forms comprising metadoxine and garlic oil as active ingredients were prepared as follows.

| Preparation Example 1: Tablet | |
|---|---|
| Metadoxine | 50 mg |
| Garlic oil | 50 mg |
| Lactose | 50 mg |
| Starch | 10 mg |
| Magnesium stearate | appropriate |

The above components were mixed and compounded into tablet according to the normal tablet making method.

| Preparation Example 2: Powder | |
|---|---|
| Metadoxine | 50 mg |
| Garlic oil | 50 mg |
| Lactose | 30 mg |
| Starch | 20 mg |
| Magnesium stearate | appropriate |

The above components were mixed well and sealed in a polyethylene-coated pouch.

| Preparation Example 3: Capsule | |
|---|---|
| Metadoxine | 50 mg |
| Garlic oil | 50 mg |
| Lactose | 30 mg |
| Starch | 28 mg |
| Talc | 2 mg |
| Magnesium stearate | appropriate |

The above components were mixed and filled in a gelatin hard capsule according to the normal capsule making method.

| Preparation Example 4: Suspension | |
|---|---|
| Metadoxine | 500 mg |
| Garlic oil | 500 mg |
| Isomerized glucose | 10 g |
| Sugar | 30 mg |
| Sodium carboxymethylcellulose | 100 mg |
| Lemon flavor | appropriate |
| Purified water to make | 100 mL |

The above components were mixed, prepared into suspension according to the normal suspension making method and put in a 100-mL brown bottle, followed by sterilization.

| Preparation Example 5: Soft capsule (contents per capsule) | |
|---|---|
| Metadoxine | 250 mg |
| Garlic oil | 250 mg |
| Polyethylene glycol 400 | 400 mg |
| Concentrated glycerin | 55 mg |
| Purified water | 35 mg |

Polyethylene glycol was mixed with concentrated glycerin, and purified water was added. Maintaining the mixture at about 60° C., metadoxine and garlic oil were added and uniformly mixed at about 1,500 rpm using a stirring machine. The mixture was slowly cooled to room temperature while slowly stirring, followed by removal of air using a vacuum pump.

The coat of the soft capsule was prepared using gelatin, 132 mg of gelatin, 52 mg of concentrated glycerin, 6 mg of 70% d-sorbitol solution, appropriate amount of ethylvanillin as fragrance and carnauba wax as coating base (contents are per capsule), according to a common method.

| Preparation Example 6: Injection (contents per ampule) | |
| --- | --- |
| Metadoxine | 50 mg |
| Garlic oil | 50 mg |
| Mannitol | 180 mg |
| Distilled water for injection | 2974 mg |
| $Na_2HPO_4 \cdot 2H_2O$ | 26 mg |

The above components were mixed in an ampule (2 mL) according to a common method.

[Industrial Applicability]

As described, the concurrent administration of metadoxine and garlic oil inhibits the accumulati on of triglyceride and increase of AST level in liver tissue caused by fatty liver, inhibits the expression of CYP2E1 and iNOS accompanied by the progress of fatty liver, and restores the activity of AMPK and ACC to normal level. Thus, the composition of the present invention comprising metadoxine and garlic oil as active ingredients may be useful in preventing and treating fatty liver induced by chronic alcohol intake and hepatitis caused thereby. Further, it may be useful in restoring or improving the liver function damaged by alcohol intake.

Although the present invention has been described in accordance with the embodiments shown, those skilled in the art will readily recognize that there could be variations to the embodiments and those variations would be within the spirit and scope of the present invention. Accordingly, many modifications may be made by those skilled in the art without departing from the spirit and scope of the appended claims.

The invention claimed is:

1. A pharmaceutical composition for treating alcohol-induced fatty liver or steatohepatitis comprising metadoxine and garlic oil as active ingredients and further comprising a pharmaceutically acceptable excipient, wherein the metadoxine and the garlic oil are comprised in the weight ratio of 1:1 to 1:3 or 1:1 to 3.

2. The pharmaceutical composition as claimed in claim 1, wherein the metadoxine and the garlic oil are comprised in the weight ratio of 1:1.

3. A pharmaceutical composition for improving or restoring the liver function damaged by alcohol intake comprising metadoxine and garlic oil as active ingredients and further comprising a pharmaceutically acceptable excipient, wherein the metadoxine and the garlic oil are comprised in the weight -ratio of 1:1 to 1:3 or 1:1 to 3:1.

4. The pharmaceutical composition as claimed in claim 3, wherein the metadoxine and the garlic oil are comprised in the weight ratio of 1:1.

5. A food composition for treating alcohol-induced fatty liver or steatohepatitis comprising metadoxine and garlic oil as active ingredients, wherein the metadoxine and he garlic oil are comprised in the weight ratio of 1:1 to 1:3 or 1:1 to 3:1.

6. A food composition for improving or restoring the liver function damaged by alcohol intake comprising metadoxine and garlic oil as active ingredients, wherein the metadoxine and the garlic oil are comprised in the weight ratio of 1:1 to 1:3 or 1:1 to 3:1.

7. A drink composition for treating alcohol-induced fatty liver or steatohepatitis comprising metadoxine and garlic oil as active ingredients, wherein the metadoxine and the garlic oil are comprised in the weight ratio of 1:1 to 1:3 or 1:1 to 3:1.

8. A drink composition for improving or restoring the liver function damaged by alcohol intake comprising metadoxine and garlic oil as active ingredients, wherein the metadoxine and the garlic oil are comprised in the weight ratio of 1:1 to 1:3 or 1:1 to 3:1.

* * * * *